(12) United States Patent
Vandenberk et al.

(10) Patent No.: US 6,348,457 B1
(45) Date of Patent: Feb. 19, 2002

(54) 4-[3-BENZOFURANYL]PIPERIDINYL AND 4-[3-BENZOTHIENYL]PIPERIDINYL DERIVATIVES

(75) Inventors: Jan Vandenberk, Beerse; Ludo Edmond Josephine Kennis, Turnhout; Albertus Henricus Maria Theresia Van Heertum, Vosselaar, all of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 08/362,529

(22) Filed: Jan. 5, 1995

Related U.S. Application Data

(62) Division of application No. PCT/EP93/01776, filed on Jul. 6, 1993, which is a continuation of application No. 07/912,936, filed on Jul. 13, 1922, now abandoned.

(51) Int. Cl.[7] .................. A61K 31/517; A61K 31/519; A61K 31/545
(52) U.S. Cl. .............. 514/214.02; 514/224.2; 514/258; 540/579; 544/48; 544/278; 544/282
(58) Field of Search .............. 544/48, 278, 282; 540/579; 574/214, 224.2, 258; 514/214.02

(56) References Cited

U.S. PATENT DOCUMENTS

| | | | |
|---|---|---|---|
| 4,342,870 A | 8/1982 | Kennis et al. | 544/282 |
| 4,443,451 A | 4/1984 | Kennis et al. | 424/251 |
| 4,804,663 A | 2/1989 | Kennis et al. | 514/258 |
| 5,140,029 A | 8/1992 | Kennis et al. | 514/272 |

FOREIGN PATENT DOCUMENTS

EP  0 453 042 A1  10/1991

*Primary Examiner*—Richard L. Raymond

(57) ABSTRACT

The invention is concerned with novel compounds of the formula

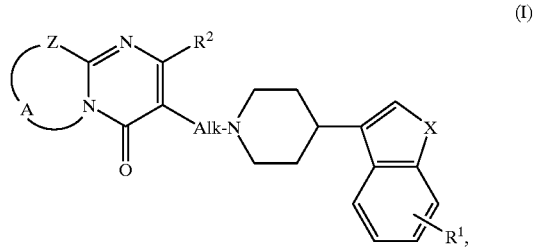

(I)

the pharmaceutically acceptable acid addition salts thereof and the stereochemically isomeric forms thereof, wherein X is oxygen or sulphur; $R^1$ is hydrogen or halo; $R^2$ is hydrogen, $C_{1-4}$alkyl, phenylmethyl or halophenylmethyl; Alk is $C_{1-4}$alkanediyl; —Z—A— is a bivalent radical selected from the group consisting of —S—$CH_2$—$CH_2$—, —S—$CH_2$—$CH_2$—$CH_2$—, —S—CH═CH—, —CH═CH—CH═CH—, —C(═$CHR^3$)—$CH_2$—$CH_2$—$CH_2$—, —CH═CH—O—, —$CHR^4$—$CH_2$—$CH_2$—, —$CHR^4$—$CH_2$—$CH_2$—$CH_2$—, —$CHR^4$—$CH_2$—$CH_2$—$CH_2$—$CH_2$—; in said bivalent radicals one hydrogen may be replaced by $C_{1-4}$alkyl; $R^3$ is phenyl or halophenyl; each $R^4$ independently represents hydrogen, hydroxy, phenylmethyl or halophenylmethyl. Pharmaceutical compositions of said compounds and use as a medicine.

2 Claims, No Drawings

4-[3-BENZOFURANYL]PIPERIDINYL AND 4-[3-BENZOTHIENYL]PIPERIDINYL DERIVATIVES

CROSS-REFERENCE TO RELATED APPLICATIONS

This application is based upon PCT application Ser. No. PCT/EP 93/01776, filed Jul. 6, 1993, which is a continuation of U.S. patent application Ser. No. 07/912,396, filed on Jul. 13, 1992, now abandoned.

BACKGROUND OF THE INVENTION

In U.S. Pat. No. 4,804,663 there are described 1,2-benzisoxazol-3-yl and 1,2-benzisothiazol-3-yl derivatives having antipsychotic and antiserotonin activity. In EP-A-0, 378,255 there are described 4-aminopyrimidinone derivatives as antagonists of the neurotransmitters serotonin and histamine. In JP-A-2-63911 there are described benzothiophene- and benzofuranderivatives as 5-HT$_2$ receptor antagonists useful for treating ischaemic heart disease, cerebrovascular disease, depression or schizophrenia. The present compounds differ structurally and show a different pharmacological profile.

DESCRIPTION OF THE INVENTION

The invention is concerned with novel compounds of the formula

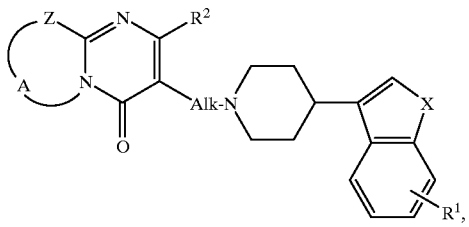

(I)

the pharmaceutically acceptable acid addition salts thereof and the stereochemically isomeric forms thereof, wherein X is oxygen or sulphur;

R$^1$ is hydrogen or halo;

R$^2$ is hydrogen, C$_{1-4}$alkyl, phenylmethyl or halophenylmethyl;

Alk is C$_{1-4}$alkanediyl;

—Z—A— is a bivalent radical selected from the group consisting of —S—CH$_2$—CH$_2$—, —S—CH$_2$—CH$_2$—CH$_2$—, —S—CH=CH—, —CH=CH—CH=CH—, —C(=CHR$^3$)—CH$_2$—CH$_2$—CH$_2$—, —CH=CH—O—, —CHR$^4$—CH$_2$—CH$_2$—, —CHR$^4$—CH$_2$—CH$_2$—CH$_2$—, —CHR$^4$—CH$_2$—CH$_2$—CH$_2$—CH$_2$—; wherein in said bivalent radicals one hydrogen may be replaced by C$_{1-4}$alkyl;

R$^3$ is phenyl or halophenyl; and each R$^4$ independently represents hydrogen, hydroxy, phenylmethyl or halophenylmethyl.

In the foregoing and hereinafter C$_{1-4}$alkanediyl defines bivalent straight and branched chain alkanediyl radicals having from 1 to 4 carbon atoms such as, for example, methylene, 1,2-ethanediyl, 1,3-propanediyl, 1,4-butanediyl and the branched isomers thereof; halo is generic to fluoro, chloro, bromo and iodo; C$_{1-4}$alkyl defines straight and branch chained saturated hydrocarbon radicals having from 1 to 4 carbon atoms such as, for example, methyl, ethyl, propyl, 1-methylethyl, butyl, 1,1-dimethylethyl, 1-methylpropyl, 2-methylpropyl and the like; and halophenylmethyl defines fluorophenylmethyl, chlorophenylmethyl, bromophenylmethyl, iodophenylmethyl and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have either the R- or the S-configuration; substituents on bivalent cyclic saturated hydrocarbon radicals may have either the cis- or trans-configuration and radicals or moieties containing double bonds may have the E- or Z-configuration. Stereochemically isomeric forms of the compounds of formula (I) are obviously intended to be embraced within the scope of this invention.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic acid and the like, sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term acid addition salt also comprises the hydrates and solvent addition forms which the compounds of formula (I) are able to form. Examples of such forms are e.g. hydrates, alcoholates and the like.

R$^1$ is suitably hydrogen or fluoro;

R$^2$ is suitably phenylmethyl or C$_{1-4}$alkyl, preferably methyl;

Alk is suitably C$_{2-3}$alkanediyl, preferably 1,2-ethanediyl or 1,3-propanediyl;

R$^3$ is suitably phenyl or fluorophenyl, especially 4-fluorophenyl;

R$^4$ is suitably hydrogen, hydroxy or halophenylmethyl, especially fluorophenylmethyl.

Particular compounds are those compounds of formula (I), wherein —Z—A— is a bivalent radical of formula —S—CH$_2$—CH$_2$—, —S—CH$_2$—CH$_2$—CH$_2$—, —S—CH=CH—, —S—CH—C(CH$_3$)—, —CH=CH—CH=CH—, —C(CH$_3$)=CH—CH=CH—, —CH=CH—O—, or —CH=C(CH$_3$)—O—.

Also particular compounds are those compounds of formula (I), wherein —Z—A— is a bivalent radical of formula —CHR$^4$—CH$_2$—CH$_2$—, —CHR$^4$—CH$_2$—CH$_2$—CH$_2$—, or —CHR$^4$—CH$_2$—CH$_2$—CH$_2$—CH$_2$—, wherein R$^4$ is hydrogen, hydroxy or halophenylmethyl, especially fluorophenylmethyl; or —C(=CHR$^3$)—CH$_2$—CH$_2$—CH$_2$—, wherein R$^3$ is phenyl or halophenyl, particularly 4-halophenyl, especially fluorophenyl, preferably 4-fluorophenyl.

A first group of particularly interesting compounds are those compounds, wherein Alk is 1,2-ethanediyl or 1,3-propanediyl, $R^4$ is hydrogen and X is oxygen or sulfur, preferably oxygen.

Another group of particularly interesting compounds are those compounds, wherein —Z—A— is a bivalent radical of formula —S—CH$_2$—CH$_2$—, —S—CH$_2$—CH$_2$—CH$_2$—, —S—CH=CH—, —CH=CH—CH=CH—, —CH$_2$—CH$_2$—CH$_2$—CH$_2$—, or —CH=C(CH$_3$)—O—.

Preferred compounds are:
6-[2-[4-(6-fluoro-3-benzofuranyl)-1-piperidinyl]ethyl]-2,3-dihydro-7-methyl-5H-thiazolo[3,2-a]pyrimidin-5-one;
3-[2-[4-(6-fluoro-3-benzofuranyl)-1-piperidinyl]ethyl]-2-methyl-4H-pyrido-[1,2-a]pyrimidin-4-one;
6-[2-[4-(6-fluoro-3-benzofuranyl)-1-piperidinyl]ethyl]-7-methyl-5H-thiazolo-[3,2-a]pyrimidin-5-one;
6-[2-[4-(6-fluoro-3-benzofuranyl)-1-piperidilyl]ethyl]-2,5-dimethyl-7H-isoxazolo-[2,3-a]pyrimidin-7-one;
6-[2-[4-(3-benzo[b]thienyl)-1-piperidinyl]ethyl]-7-methyl-5H-thiazolo[3,2-a]pyrimidin-5-one;
3-[2-[4-(3-benzo[b]thienyl)-1-piperidinyl]ethyl]-6,7,8,9-tetrahydro-2-methyl-4H-pyrido[1,2-a]pyrimidin-4-one;
3-[2-[4-(3-benzo[b]thienyl)-1-piperidinyl]ethyl]-2,9-dimethyl-4H-pyrido-[1,2-a]pyrimidin-4-one;
3-[3-[4-(6-fluoro-3-benzofuranyl)-1-piperidinyl]propyl]-2,9-dimethyl-4H-pyrido-[1,2-a]pyrimidin-4-one;
3-[2-[4-(6-fluoro-3-benzofuranyl)-1-piperidinyl]ethyl]-2-(phenylmethyl)-4H-pyrido-[1,2-a]pyrimidin-4-one, the stereochemically isomeric forms and the pharmaceutically acceptable acid addition salts thereof.

Most preferred compounds are:
3-[2-[4-(6-fluoro-3-benzofuranyl)-1-piperidinyl]ethyl]-2-methyl-4H-pyrido-[1,2-a]pyrimidin-4-one,
6-[2-[4-(6-fluoro-3-benzofuranyl)-1-piperidinyl]ethyl]-7-methyl-5H-thiazolo-[3,2-a]pyrimidin-5-one and the pharmaceutically acceptable acid-addition salts thereof.

The compounds of formula (I) can generally be prepared by N-alkylating an intermediate of formula (II) with an intermediate of formula (III). In formula (III) and the formulae hereinafter, $W^1$ represents a reactive leaving group such as, for example, halo, e.g. chloro, bromo or iodo, or a sulfonyloxygroup, e.g. methanesulfonyloxy, 4-methylbenzenesulphonyloxy and the like.

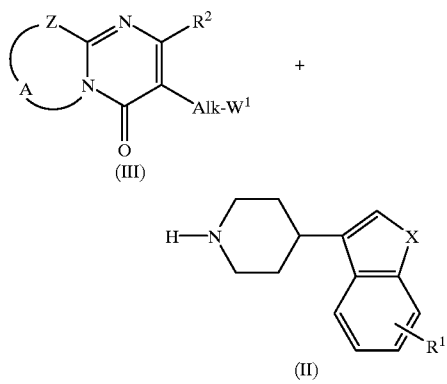

The reaction of (II) with (III) can conveniently be conducted in a reaction-inert organic solvent such as, for example, an aromatic hydrocarbon, e.g. benzene, methylbenzene, dimethylbenzene and the like; a lower alkanol, e.g. methanol, ethanol, 1-butanol and the like; a ketone, e.g. 2-propanone, 4-methyl-2-pentanone and the like; an ether, e.g. 1,4-dioxane, 1,1'-oxybisethane, tetrahydrofuran and the like; N,N-dimethylformamide, N,N-dimethylacetamide, nitrobenzene, 1-methyl-2-pyrrolidinone and the like. The addition of an appropriate base such as, for example, an alkali or an earth alkaline metal carbonate, hydrogen carbonate, hydroxide, alkoxide or hydride, e.g. sodium carbonate, sodium hydrogen carbonate, potassium carbonate, sodium hydroxide, sodium methoxide, sodium hydride and the like, or an organic base such as, for example, a tertiairy amine, e.g. N,N-diethylethanamine, N-(1-methylethyl)-2-propanamine, 4-ethylmorpholine and the like, may be useful to pick up the acid which is liberated during the course of the reaction. In some circumstances the addition of a iodide salt, preferably an alkali metal iodide, is appropriate. Somewhat elevated temperatures may enhance the rate of the reaction.

The compounds of formula (I), can also be prepared following art-known cyclizing procedures for preparing pyrimidin-4-ones such as, for example, by reacting an amine of formula (IV) with a β-dicarbonyl derivative of formula (V) or by cyclizing a reagent of formula (VI) with an enamine of formula (VII). In formula (V) and in the formulae hereinafter each $W^2$ independently represents an appropriate leaving group such as, for example, hydroxy, halo, $C_{1-4}$alkyloxy, $C_{1-4}$alkylcarbonyloxy, amino, mono- or di($C_{1-4}$alkyl)amino.

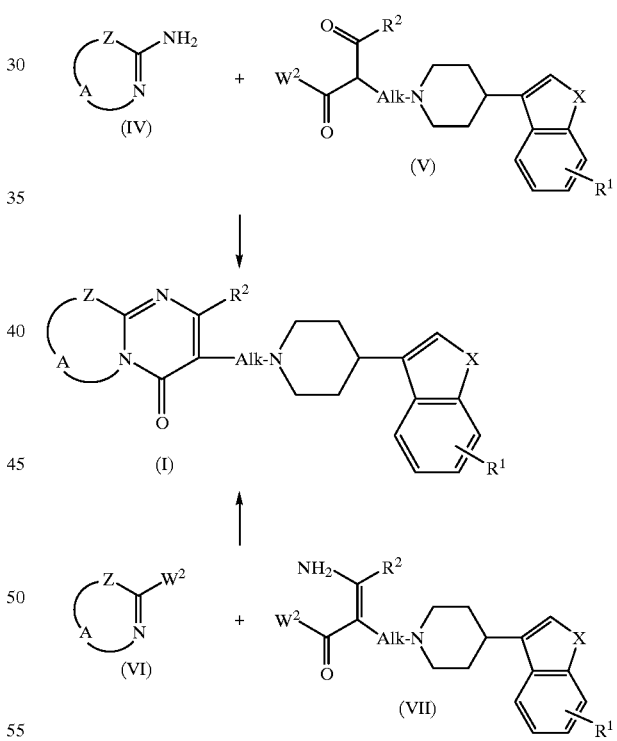

Said cyclization reactions may generally be carried out by stirring the reactants, optionally in the presence of a suitable reaction-inert solvent such as, for example, an aliphatic, alicyclic or aromatic hydrocarbon, e.g. hexane, cyclohexane or benzene and the like; or pyridine, N,N-dimethylformamide and the like dipolar aprotic solvents. Elevated temperatures may be appropriate to enhance the reaction rate; more in particular it may be advantageous to carry out the reaction at the reflux temperature of the reaction mixture.

Following the same procedure the compounds of formula (I) can also be prepared by cyclizing an intermediate of formula (VII) with a reagent of formula (VIII).

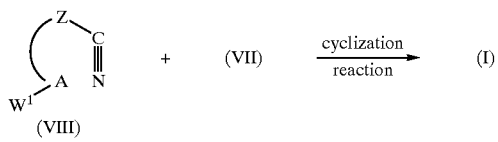

The compounds of formula (I) wherein Z—A is a bivalent radical —S—CH$_2$—CH$_2$— or —S—CH$_2$—CH$_2$—CH$_2$— and wherein in said bivalent radicals one hydrogen may be replaced by C$_{1-4}$alkyl, said compounds being represented by the formula (I-a), can also be prepared by cyclizing a 2-mercaptopyrimidinone of formula (IX) with a reagent of formula (X), wherein n is 2 or 3 and wherein one hydrogen may be replaced by C$_{1-4}$alkyl.

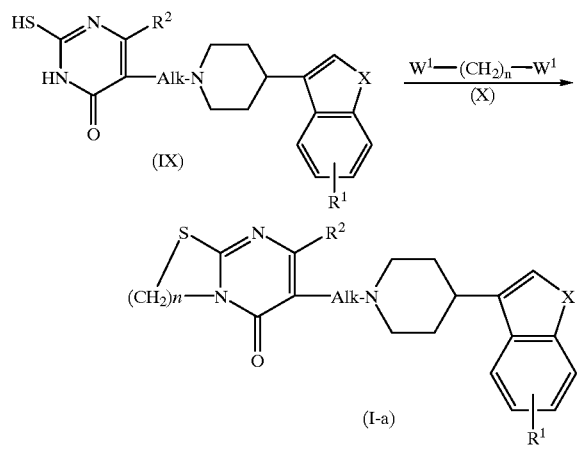

The compounds of formula (I) wherein Z—A is a bivalent radical of formula —S—CH=CH—, wherein one hydrogen may be replaced by C$_{1-4}$alkyl, said compounds being represented by the formula (I-b), can be prepared by cyclizing a 2-mercapto-pyrimidinone of formula (IX) with a reagent of formula (XI) wherein one hydrogen atom may be replaced by C$_{1-4}$alkyl.

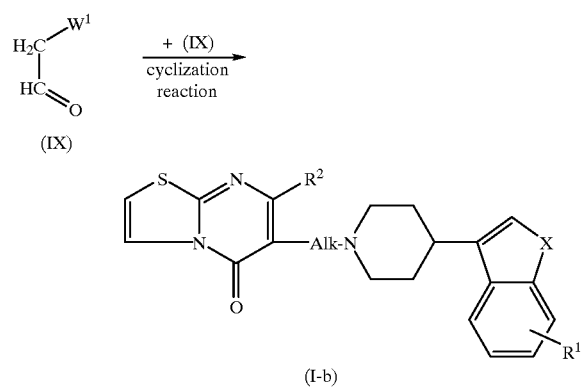

Said cyclization reactions for preparing the compounds of formulae (I-a) and (I-b) may generally be carried out by stirring the reactants, if desired, in the presence of a suitable reaction-inert solvent such as, for example, an aliphatic, alicyclic or aromatic hydrocarbon, e.g. hexane, cyclohexane or benzene and the like; or pyridine, N,N-dimethylfornamide and the like dipolar aprotic solvents. Elevated temperatures may be appropriate to enhance the reaction-rate, more in particular it may be preferred to carry out the reaction at the reflux temperature of the reaction mixture.

The compounds of formula (I) may also be converted into each other using art-known functional group transformations. For example, compounds of formula (I), wherein R$^1$ is hydrogen may be converted into compounds of formula (I) wherein R$^1$ is halo using art-known halogenation techniques.

A number of intermediates and starting materials in the foregoing preparations are known compounds which may be prepared according to art-known methodologies of preparing said or similar compounds. The intermediates of formula (III) and their preparations are described in U.S. Pat. No. 4,804,663 and in the references cited therein.

The intermediates of formula (II) wherein X is oxygen, said intermediates being represented by formula (II-a), can be prepared by cyclizing an aldehyde of formula (XII) and deprotecting the intermediate of formula (XIII). In formula (XII) and the formulae hereinunder P represents a protective group such as for example C$_{1-6}$alkylcarbonyl and W$^3$ represent a reactive leaving group such as, for example, halo, e.g. fluoro, chloro, bromo, iodo.

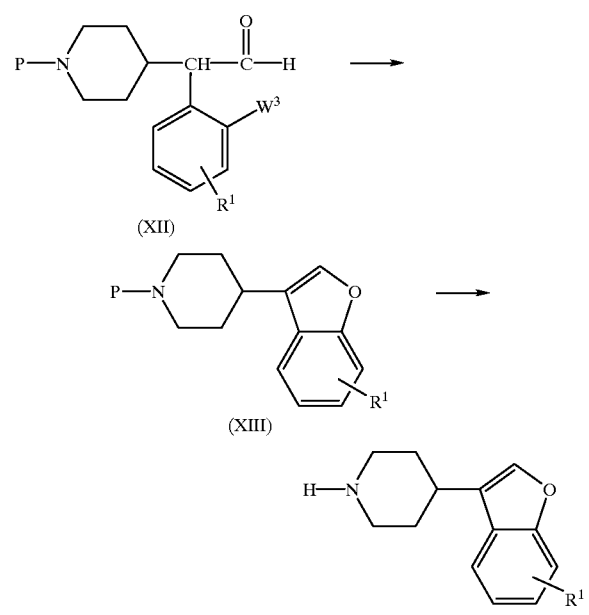

Said cyclization may conveniently be conducted by treating the aldehyde of formula (XII) with an appropriate base in an reaction-inert organic solvent such as, for example, an aromatic hydrocarbon, e.g. benzene, methylbenzene, dimethylbenzene and the like, an ether, e.g. 1,4-dioxane, 1,1'-oxybisethane, tetrahydrofuran and like; a dipolar aprotic solvent, such as, for example N,N-dimethylformamide, N N-dimethylacetamide and the like. Appropriate bases are for example alkali or earth alkaline metal carbonate, hydrogen carbonate, hydroxide, alkoxide, hydride, e.g. sodium carbonate, sodium hydrogen carbonate, potassium carbonate, sodium hydroxide, sodium methoxide, sodium hydride and the like, or an organic base such as a tertiary amine, e.g. N,N-ethylethanamine, N-(1-methylethyl)-2-propanamine, 4-ethylmorpholine and the like.

The intermediate aldehyde of formula (XII) can be prepared by reacting an epoxide of formula (XIV) with an acid, such as, for example, a mineral acid, e.g. perchloric acid, sulphuric acid and the like; a Lewis acid, e.g. borontrifluoride, magnesiumdibromide, aluminiumtrichloride and the like in an appropriate solvent.

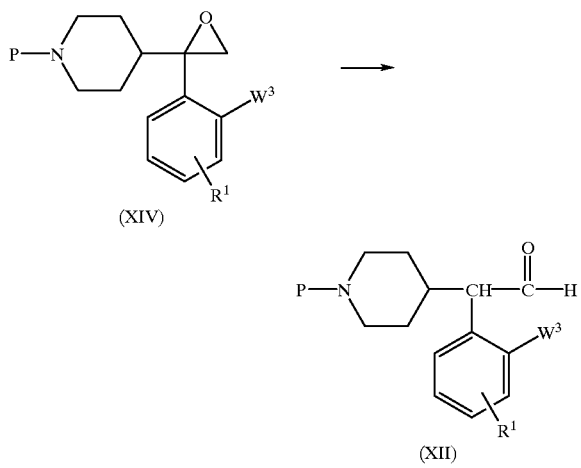

Depending upon the nature of the acid, appropriate solvents are water; alkanols, e.g. methanol, ethanol and the like; aromatic hydrocarbons, e.g. benzene, methylbenzene, dimethylbenzene and the like; ethers, e.g. 1,1'oxybisethane, tetrahydrofuran and the like; halogenated hydrocarbons, e.g. dichloromethane, trichloromethane and the like. Stirring and elevated temperatures may enhance the rate of the reaction.

The epoxides of formula (XIV) can be obtained by stirring a ketone of formula (XV) with a sulphur ylide, such as dimethyloxosulfonium methylide or dimethylsulfonium methylide in an appropriate solvent, such as, for example, an ether, e.g. 1,1'-oxybisethane, tetrahydrofuran, 2,2'-oxybispropane and the like; a dipolar aprotic solvent, e.g. dimethylsulfoxide, N,N-dimethylacetamide, N,N-dimethylformamide and the like.

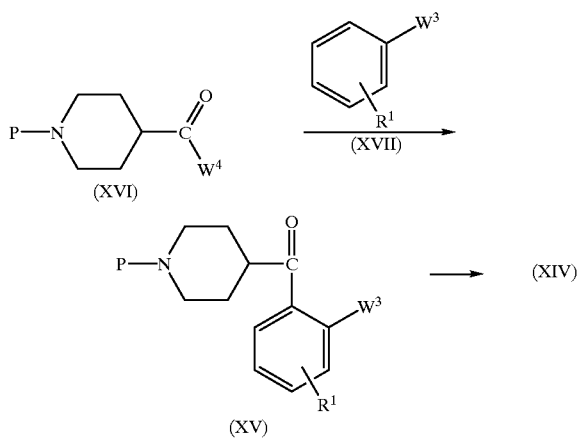

The ketones of formula (XV) can be prepared by a Friedel-Crafts acylation of piperidines of formula (XVI) wherein $W^4$ is a reactive leaving group such as for example hydroxy, halo, $C_{1-4}$carbonyloxy and the like, with benzene-derivative of formula (XVII). Said Friedel-Crafts acylation can be performed by stirring the reactants in the presence of an acid in a reaction-inert solvent, such as for example, an ether, e.g. 1,1'-oxybisethane, 2,2'oxybispropane, tetrahydrofuran, dioxane and the like, a halogenated hydrocarbon, e.g. dichloromethane, trichloromethane and the like. Suitable acids are mineral acids such as sulphuric acid, phosphoric acid, phosphorous pentoxide and the like, Lewis acids, e.g. aluminiumtrichloride, ferric chloride, zinc chloride and the like.

The compounds of formula (I) and the pharmaceutically acceptable acid addition salts have useful pharmacological properties. For example, the compounds of formula (I) possess anti-dopamine activity and show good affinity for several serotonin receptors, especially $5HT_{1A}$. Said compounds can also inhibit neuronal serotonin reuptake. Furthermore the compounds of formula (I) antagonize the action of reserpine (cfr. Example 3). Due to their pharmacological activities, the compounds of formula (I) and their pharmaceutically acceptable acid addition salts can be used in the treatment of psychotic diseases and in the treatment of a variety of complaints in which serotonin is of predominant importance. The present compounds may block serotonin-induced contractions of bronchial tissues and of blood vessels, arteries as well as veins. Particularly in view of their reserpine-antagonizing activity the compounds of formula (I) also have useful properties as anti-depressants, anxiolytics, antitremor agents and show activity against obsessive compulsive disorders, such as anorexia, bulimia and addiction, e.g. alcohol abuse.

The compounds of the present invention therefore may be used as medicines against above-mentioned conditions. Said use as a medicine or method of treatment comprises the systemic administration to patients of an amount effective to combat the conditions such as depression, anxiety, obsessive compulsive disorders, tremor and the like.

The subject compounds may be formulated into various pharmaceutical forms for administration purposes. Said pharmaceutical forms or compositions are deemed novel and consequently constitute another aspect of the present invention. Also the preparation of said compositions constitutes a further aspect of the present invention. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employee In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdernal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the usefulness of the subject compounds in the treatment of neurotransmitter mediated diseases it is evident that the present invention provides a method of treating warm-blooded animals suffering from such diseases, said method comprising the systemic administration of a pharmaceutically effective amount of a compound of formula (I) or a pharmaceutically acceptable acid addition salt thereof in admixture with a pharmaceutical carrier. Those of skill in the treatment of diseases associated with neurotransmitters could easily determine the effective amount. In general it is contemplated that an effective amount would be from 0.01 mg/kg to 4 mg/kg body weight, preferably from 0.04 mg/kg to 2 mg/kg body weight.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention in all its aspects. Unless otherwise stated all parts therein are by weight.

EXPERIMENTAL PART

A. Preparation of Intermediates

Example 1 a) To a stirred of mixture of 56 ml of 1,3-difluorobenzene, 130 g of aluminium chloride and 147 ml of dichloromethane, a solution of 95 g of 1-acetyl-4-piperidinecarbonyl chloride in 50 ml of dichloromethane was added dropwise while cooling. Upon completion, stirring was continued for 3 hours at room temperature. The reaction mixture was poured out into a mixture of crushed ice and hydrochloric acid. The product was extracted with dichloromethane. The organic layer was dried, filtered and evaporated, yielding 48 g (36%) of 1-acetyl-4-(2,4-difluorobenzoyl)piperidine as a residue (interm. 1).

b) 31.2 g of a dispersion of sodium hydride in mineral oil (50%) under a nitrogen atmosphere was washed twice with petroleum ether. There were added 230 ml of dimethyl sulfoxide. After stirring for 45 minutes at 70–75° C., the reaction mixture was cooled to a temperature of about 10° C. Then a suspension of 143 g of trimethyl-sulfoxonium iodide in 100 ml of dimethyl sulfoxide was added. The whole was stirred for 5 minutes and there was added a suspension of 135 g of intermediate (1) in 170 ml of tetrahydrofuran. The temperature was rised to 25–35° C., and the reaction mixture was stirred for 2 hours at room temperature. The reaction mixture was poured out into crushed ice and the product was extracted with 2,2'-oxybispropane. The extract was stirred with activated charcoal, dried, filtered and evaporated, yielding 96 g (68.3%) of 1-acetyl-4-[2-(2,4-difluorophenyl)oxiranyl]piperidine as an oily residue (intermn. 2).

c) To a mixture of 96 g of intermediate (2) and 24.2 g of boron trifluoride etherate at room temperature were added 700 ml of benzene. After stirring for 45 minutes at reflux temperature, the reaction mixture was cooled and washed twice with 400 ml of water. The organic layer was separated and stirred with activated charcoal, dried, filtered and evaporated, yielding 80 g (83.6%) of 1-acetyl-α-(2,4-difluorophenyl)-4-piperidine-acetaldehyde (interm. 3).

d) 2.4 g of a dispersion of sodium hydride in mineral oil (50%) under a nitrogen atmosphere was washed twice with petroleum ether. There were added 60 ml of N,N-dimethylformamide. The whole was stirred at room temperature and a solution of 11.2 g of intermediate (3) in 40 ml of N,N-dimethylformamide was added dropwise. After stirring for 3 hours at 100–105° C., the reaction mixture was evaporated and the residue was stirred in water. The product was extracted with dichloromethane. The extract was separated, dried, filtered and evaporated. The residue was stirred in acetonitrile and mixed with activated charcoal. The whole was filtered and the filtrate was evaporated, yielding 9 g (86.1%) of 1-acetyl-4-(6-fluoro-3-benzofuranyl)piperidine (interm. 4).

e) A mixture of 63 g intermediate (4) in 630 ml of hydrochloric acid 6N was stirred for 3 hours at reflux temperature. After cooling, the reaction mixture was washed with methylbenzene. The mixture was stirred at room temperature and a precipitate was formed. The precipitate was filtered off and washed with some 2-propanone and dried, yielding 34 g (55.4%) of product (fraction 1). The filtrate was evaporated and the residual oil was dissolved in 2-propanone. This solution was stirred at room temperature and a precipitate was formed, yielding 9 g (15%) of product (fraction 2). Total yield: 43 g (70.4%) of 4-(6-fluoro-3-benzofuranyl)piperidine hydrochloride; mp. 238.1° C.; (interm. 5).

B. Preparation of Final Compounds

Example 2

A mixture of 3.8 g of 3-(2-chloroethyl)-2-methyl-4H-pyrido[1,2-a]pyrimidin-4-one, 3.8 g of intermediate (5), 10 g of sodium carbonate and a few crystals of potassium iodide in 180 ml of 4-methyl-2-pentanone was stirred overnight at reflux temperature. After cooling, the reaction mixture was poured out into water. The separated organic layer was dried, filtered and evaporated. The residue was purified by column chromatography over silica gel (eluent: $CH_2Cl_2/CH_3OH$ 95/5). The pure fractions were collected and the eluent was evaporated. The residue was crystallized from acetonitrile. The product was filtered off and dried, yielding 3.8 g (62.5%) of 3-[2-[4-(6-fluoro-3-benzofuranyl)-1-piperidinyl]ethyl]-2-methyl-4H-pyrido-[1,2-a]pyrimidin-4-one; mp. 159.8° C.; (comp. 1).

In this manner were prepared:

films were connected to an amplifier. The test cage was situated in a sound and light attenuating out box, being constantly illuminated and air-ventilated. The piezo-electric response, produced by deformation of the cage floor was amplified by an individual amplifier for each piezo-film separately. The sum of these signals was observed by a noise detection system which prevented further transmission if the

TABLE 1

| Co. No. | —Z—A— | $R^2$ | n | X | $R^1$ | mp. |
|---|---|---|---|---|---|---|
| 1 | —CH=CH—CH=CH— | $CH_3$ | 2 | O | 6-F | 159.8° C. |
| 2 | —$(CH_2)_4$— | $CH_3$ | 2 | O | 6-F | 164.7° C. |
| 3 | —S—$(CH_2)_2$— | $CH_3$ | 2 | O | 6-F | 192.5° C. |
| 4 | —S—CH=CH— | $CH_3$ | 2 | O | 6-F | 161.1° C. |
| 5 | —CH=C($CH_3$)—O— | $CH_3$ | 2 | O | 6-F | 150.8° C. |
| 6 | —S—CH=CH— | $CH_3$ | 2 | S | H | 135.8° C. |
| 7 | —$(CH_2)_4$— | $CH_3$ | 2 | S | H | 122.8° C. |
| 8 | —C($CH_3$)=CH—CH=CH— | $CH_3$ | 2 | S | H | 161.3° C. |
| 9 | —S—CH=C($CH_3$)— | $CH_3$ | 3 | O | 6-F | 216.9° C. * |
| 10 | —S—$(CH_2)_3$— | $CH_3$ | 3 | O | 6-F | 198.9° C. * |
| 11 | —S—$(CH_2)_2$— | $CH_3$ | 3 | O | 6-F | 204.1° C. * |
| 12 | —C(=CH—$C_6H_5$)—$(CH_2)_3$— | $CH_3$ | 2 | O | 6-F | 135.9° C. (E) |
| 13 | —S—CH=CH— | $CH_3$ | 3 | O | 6-F | 186.9° C. * |
| 14 | —C($CH_3$)=CH—CH=CH— | $CH_3$ | 3 | O | 6-F | 104.7° C. |
| 15 | —C[=CH—(4-F—$C_6H_4$)]—$(CH_2)_3$— | $CH_3$ | 2 | O | 6-F | 189.4° C. (E) |
| 16 | —CH[—$CH_2$—(4-F—$C_6H_4$)]—$(CH_2)_3$— | $CH_3$ | 2 | O | 6-F | 185.8° C. |
| 17 | —$(CH)_4$— | —$CH_2$—$C_6H_5$ | 2 | O | 6-F | 158.7° C. |

* = (E)-2-butenedioate (1:1)

C. Pharmacological Example

Example 3

Reserpine Tremor Test

Female Wistar rats weighing 200–220 g were used. These test animals were food deprived for 24 hours. Said rats were pretreated orally (po) or subcutaneously (sc) with a test compound at 90 minutes before testing. This pretreatment was followed by an intravenous injection of 2 mg/kg reserpine at 60 minutes before testing. Two control groups of 20 rats each were included in the experiment. The first control group consisted of rats that were only treated with a saline solution and the second control group consisted of animals which only received a saline reserpine solution. At the start of the test, the rats were individually placed in specially designed test cages and tremor activity was measured continuously during a 15-min test session. These test cages consisted of a plexiglass chamber. The floor of the test cage consisted of a plexiglass plate which was centered underneath the cage. The cage did not support onto this floor plate. The floor plate rested at its four corners on a rubber point of support. Two pieces of piezo-film were tied up next to each other underneath the middle of the floor plate. Said piezo-signal was below the selected noise level of 100 mVolt. The tremor count in these experiments represented the appearance of 10 successive electrical signals that, after having been amplified and filtered, all exceeded a trigger level of 100 mVolt and differed no more than 400 mVolt from each other. The average activity of the control group that only received a saline solution was about 34 and the tremor activity of the reserpine treated control group was about 152 counts. On this basis, a compound was deemed active at a certain dose if the tremor activity is below 35 counts and deemed inactive when the tremor activity was above said count level. The activity of compounds are shown in Table 2.

TABLE 2

| Co No | route | dose (mg/kg) | rats showing a tremor activity below 35 counts | rats tested |
|---|---|---|---|---|
| 1 | sc | 2.5 | 3 | 3 |
| 2 | sc | 2.5 | 2 | 2 |
| 4 | sc | 2.5 | 3 | 3 |
| 5 | sc | 2.5 | 2 | 2 |
| 9 | po | 2.5 | 2 | 2 |

D. Composition Examples

"Active ingredient" (A.I.) as used throughout these examples relates to a compound of formula (I), a pharmaceutically acceptable acid addition salt or a stereochemically isomeric form thereof.

Example 4

Oral Drops

500 Grams of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example 5

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example 6

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

Example 7

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10,000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example 8

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I . The solution was cooled to room temperature and supplemented with water for injection q.s. ad 1 l, giving a solution comprising 4 mg/ml of A.I. The solution was sterilized by filtration and filled in sterile containers.

Example 9

Suppositories

3 Grams A.I. was dissolved in a solution of 3 grams 2,3-dihydroxybutanedioic acid in 25 ml polyethylene glycol 400. 12 Grams surfalctant and triglycerides q.s. ad 300 grams were molten together. The latter mixture was mixed well with the former solution. The thus obtained mixture was poured into moulds at a temperature of 37–38° C. to form 100 suppositories each containing 30 mg/ml of the A.I.

Example 10

Injectable Solution

60 Grams of A.I. and 12 grams of benzylalcohol were mixed well and sesame oil was added q.s. ad 1 l, giving a solution comprising 60 mg/ml of A.I. The solution was sterilized and filled in sterile containers.

What is claimed is:

1. A method of antagonizing the action of reserpine in warm blooded animals which comprises the administration to warm blooded animals of a therapeutically effective amount of a compound of the formula:

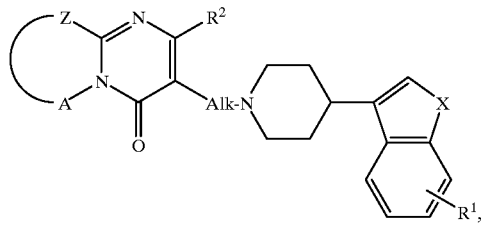

a pharmaceutically acceptable acid addition salt thereof or a stereochemically isomeric form thereof, wherein:

X is oxygen or sulfur;

$R^1$ is hydrogen or halo;

$R^2$ is hydrogen, $C_{1-4}$alkyl, phenyl methyl or halophenylmethyl;

Alk is $C_{1-4}$alkanediyl; and

—Z—A— is a bivalent radical selected from the group consisting of —S—$CH_2$—$CH_2$—, —S—$CH_2$—$CH_2$—

$CH_2$—, —S—CH=CH—, —CH=CH—CH=CH—, —C(=CHR$^3$)—CH$_2$—CH$_2$—CH$_2$—, —CH=CH—O—, —CHR$^4$—CH$_2$—CH$_2$—, —CHR$^4$—CH$_2$—CH$_2$—CH$_2$—, and —CHR$^4$—CH$_2$—CH$_2$—CH$_2$—CH$_2$—;

wherein in said bivalent radicals:
one hydrogen may be replaced by C$_{1-4}$alkyl;
R$^3$ is phenyl or halo phenyl; and
each R$^4$ independently represents hydrogen, hydroxy, phenylmethyl or halophenylmethyl.

2. A method of antagonizing the action of dopamine in warm blooded animals which comprises the administration to warm blooded animals of a therapeutically effective amount of a compound of the formula:

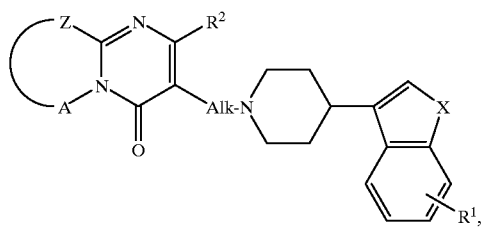

(I)

a pharmaceutically acceptable acid addition salt thereof or a stereochemically isomeric form thereof, wherein:

X is oxygen or sulfur;

R$^1$ is hydrogen or halo;

R$^2$ is hydrogen, C$_{1-4}$alkyl, phenyl methyl or halophenyl-methyl;

Alk is C$_{1-4}$alkanediyl; and

—Z—A— is a bivalent radical selected from the group consisting of —S—CH$_2$—CH$_2$—, —S—CH$_2$—CH$_2$—CH$_2$—, —S—CH=CH—, —CH=CH—CH=CH—, —C(=CHR$^3$)—CH$_2$—CH$_2$—CH$_2$—, —CH=CH—O—, —CHR$^4$—CH$_2$—CH$_2$—, —CHR$^4$—CH$_2$—CH$_2$—CH$_2$—, and —CHR$^4$—CH$_2$—CH$_2$—CH$_2$—CH$_2$—;

wherein in said bivalent radicals:
one hydrogen may be replaced by C$_{1-4}$alkyl;
R$^3$ is phenyl or halo phenyl; and
each R$^4$ independently represents hydrogen, hydroxy, phenylmethyl or halophenylmethyl.

\* \* \* \* \*